United States Patent
Dickens et al.

(10) Patent No.: US 10,945,463 B2
(45) Date of Patent: Mar. 16, 2021

(54) ELECTRONIC AEROSOL PROVISION SYSTEM WITH MULTIPLE MODES BASED ON SENSED EVENTS

(71) Applicant: c/o Nicoventures Holdings Limited, London (GB)

(72) Inventors: Colin Dickens, London (GB); Rory Fraser, London (GB)

(73) Assignee: NICOVENTURES HOLDINGS LIMITED, London (GB)

( * ) Notice: Subject to any disclaimer, the term of this patent is extended or adjusted under 35 U.S.C. 154(b) by 0 days.

(21) Appl. No.: 15/739,019

(22) PCT Filed: Jun. 10, 2016

(86) PCT No.: PCT/GB2016/051729
§ 371 (c)(1),
(2) Date: Dec. 21, 2017

(87) PCT Pub. No.: WO2017/001817
PCT Pub. Date: Jan. 5, 2017

(65) Prior Publication Data
US 2018/0184711 A1    Jul. 5, 2018

(30) Foreign Application Priority Data
Jul. 1, 2015  (GB) ...................................... 1511566

(51) Int. Cl.
*A24F 13/00*    (2006.01)
*A24F 47/00*    (2020.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC ....................................................... A24F 47/00
(Continued)

(56) References Cited

U.S. PATENT DOCUMENTS

| | | | |
|---|---|---|---|
| 2,057,353 A | 10/1936 | Whittemore, Jr. |
| 4,947,875 A | 8/1990 | Brooks et al. |

(Continued)

FOREIGN PATENT DOCUMENTS

| | | |
|---|---|---|
| CA | 2641869 A1 | 5/2010 |
| CA | 2876267 A1 | 6/2015 |

(Continued)

OTHER PUBLICATIONS

Great Britain Search Report, Application No. GB1511566.3, dated Nov. 30, 2015, 4 pages.

(Continued)

*Primary Examiner* — Phuong K Dinh
(74) *Attorney, Agent, or Firm* — Patterson Thuente Pedersen, P.A.

(57) ABSTRACT

Aerosol delivery devices disclosed herein seek to help address or reduce some of the issues associated with accidental/unintended activation of an aerosol delivery device. This is done in some example implementations by control circuitry controlling when an aerosol delivery device switches between different modes based on signaling received from a motion sensor and an airflow sensor. The control circuitry can determine from motion detection signals when there is a tapping event corresponding to the device being tapped by a user and to determine from airflow detection signals when there is an airflow event corresponding a flow of air in the device.

21 Claims, 3 Drawing Sheets

(51) Int. Cl.
  *A61M 11/04* (2006.01)
  *A61M 15/06* (2006.01)
  *G05B 19/406* (2006.01)
  *H05B 1/02* (2006.01)
  *A61M 16/00* (2006.01)

(52) U.S. Cl.
  CPC ......... *G05B 19/406* (2013.01); *H05B 1/0297* (2013.01); *A61M 2016/0015* (2013.01); *A61M 2016/0027* (2013.01); *A61M 2205/332* (2013.01); *A61M 2205/3334* (2013.01); *A61M 2205/3653* (2013.01); *A61M 2205/50* (2013.01); *A61M 2205/8206* (2013.01); *G05B 2219/37371* (2013.01)

(58) Field of Classification Search
  USPC .................................................. 131/328–329
  See application file for complete search history.

(56) References Cited

U.S. PATENT DOCUMENTS

| | | | |
|---|---|---|---|
| 5,095,921 A | 3/1992 | Losee et al. | |
| 5,261,424 A | 11/1993 | Sprinkel | |
| 5,372,148 A | 12/1994 | McCafferty et al. | |
| 5,809,997 A | 9/1998 | Wolf | |
| 5,894,841 A | 4/1999 | Voges | |
| 5,949,632 A | 9/1999 | Barreras | |
| 6,183,425 B1 | 2/2001 | Whalen | |
| 6,196,218 B1 | 3/2001 | Voges | |
| 6,958,691 B1 | 10/2005 | Anderson et al. | |
| 7,109,445 B2 | 9/2006 | Patterson | |
| 7,726,320 B2 | 6/2010 | Robinson | |
| 7,726,329 B2 | 6/2010 | Robinson | |
| 8,550,069 B2 | 10/2013 | Alelov | |
| 8,807,131 B1 | 8/2014 | Tunnell | |
| 8,997,753 B2 | 4/2015 | Li | |
| 9,095,175 B2 | 8/2015 | Terry et al. | |
| 9,289,014 B2 | 3/2016 | Tucker | |
| 9,451,791 B2 | 9/2016 | Sears | |
| 9,462,832 B2 | 10/2016 | Lord | |
| 9,497,999 B2 | 11/2016 | Lord | |
| 9,597,466 B2 | 3/2017 | Henry | |
| 10,159,279 B2 | 12/2018 | Lord | |
| 2003/0033055 A1 | 2/2003 | McRae et al. | |
| 2003/0123328 A1 | 7/2003 | Guanter | |
| 2003/0179003 A1 | 9/2003 | Toda et al. | |
| 2003/0226837 A1 | 12/2003 | Blake | |
| 2005/0045193 A1 | 3/2005 | Yang | |
| 2005/0058441 A1 | 3/2005 | Kameyama et al. | |
| 2005/0081846 A1 | 4/2005 | Barney | |
| 2005/0143866 A1 | 6/2005 | McRae | |
| 2005/0161467 A1 | 7/2005 | Jones | |
| 2005/0247305 A1 | 11/2005 | Zierenberg | |
| 2005/0268911 A1 | 12/2005 | Cross et al. | |
| 2006/0047368 A1 | 3/2006 | Maharajh | |
| 2006/0130838 A1 | 6/2006 | Yong | |
| 2007/0006889 A1 | 1/2007 | Kobal | |
| 2007/0045288 A1 | 3/2007 | Nelson | |
| 2008/0092912 A1 | 4/2008 | Robinson et al. | |
| 2008/0257367 A1 | 10/2008 | Paterno | |
| 2009/0230117 A1 | 9/2009 | Fernando et al. | |
| 2009/0283103 A1 | 11/2009 | Nielsen | |
| 2009/0308387 A1 | 12/2009 | Andersen | |
| 2010/0050770 A1 | 3/2010 | Barger | |
| 2010/0059070 A1 | 3/2010 | Potter et al. | |
| 2010/0206306 A1 | 8/2010 | Feriani | |
| 2010/0242974 A1 | 9/2010 | Pan | |
| 2011/0036346 A1 | 2/2011 | Cohen | |
| 2011/0113368 A1 | 5/2011 | Carvajal | |
| 2011/0210746 A1 | 9/2011 | Yogou et al. | |
| 2011/0226236 A1 | 9/2011 | Buchberger | |
| 2011/0247620 A1 | 10/2011 | Armstrong | |
| 2011/0253139 A1 | 10/2011 | Guthrie | |
| 2011/0265806 A1 | 11/2011 | Alarcon et al. | |
| 2012/0012106 A1 | 1/2012 | Bari | |
| 2012/0048266 A1 | 3/2012 | Alelov | |
| 2012/0186594 A1 | 7/2012 | Liu | |
| 2012/0208601 A1 | 8/2012 | Lockwood | |
| 2012/0318882 A1 | 12/2012 | Abehasera | |
| 2013/0008436 A1 | 1/2013 | Von Hollen | |
| 2013/0042865 A1 | 2/2013 | Monsees | |
| 2013/0104916 A1 | 5/2013 | Bellinger | |
| 2013/0192615 A1 | 8/2013 | Tucker | |
| 2013/0199528 A1 | 8/2013 | Goodman | |
| 2013/0228191 A1 | 9/2013 | Newton | |
| 2013/0255702 A1 | 10/2013 | Griffith | |
| 2013/0269685 A1 | 10/2013 | Wachtel | |
| 2013/0284192 A1 | 10/2013 | Peleg | |
| 2013/0319439 A1 | 12/2013 | Gorelick | |
| 2013/0340775 A1 | 12/2013 | Juster | |
| 2014/0000603 A1 | 1/2014 | Hosemann | |
| 2014/0000638 A1 | 1/2014 | Sebastian | |
| 2014/0008384 A1 | 1/2014 | Helmlinger | |
| 2014/0060554 A1 | 3/2014 | Collett | |
| 2014/0096781 A1 | 4/2014 | Sears | |
| 2014/0123990 A1 | 5/2014 | Timmermans | |
| 2014/0209105 A1* | 7/2014 | Sears .................. F22B 1/28 131/328 |
| 2014/0261414 A1 | 9/2014 | Weitzel | |
| 2014/0261486 A1 | 9/2014 | Potter | |
| 2014/0270727 A1 | 9/2014 | Ampolini | |
| 2014/0345635 A1 | 11/2014 | Rabinowitz | |
| 2014/0366898 A1 | 12/2014 | Monsees | |
| 2015/0047656 A1 | 2/2015 | Robinson | |
| 2015/0097513 A1 | 4/2015 | Liberi | |
| 2015/0114408 A1 | 4/2015 | Lord | |
| 2015/0128965 A1 | 5/2015 | Lord | |
| 2015/0128966 A1 | 5/2015 | Lord | |
| 2015/0136153 A1 | 5/2015 | Lord | |
| 2015/0237917 A1 | 8/2015 | Lord | |
| 2015/0245660 A1 | 9/2015 | Lord | |
| 2015/0257448 A1 | 9/2015 | Lord | |
| 2015/0336689 A1 | 11/2015 | Brown et al. | |
| 2016/0206000 A1 | 7/2016 | Lord et al. | |
| 2016/0242466 A1 | 8/2016 | Lord et al. | |
| 2017/0035114 A1 | 2/2017 | Lord | |
| 2019/0133192 A1 | 5/2019 | Lord | |

FOREIGN PATENT DOCUMENTS

| | | |
|---|---|---|
| CA | 2876267 A1 | 6/2015 |
| CN | 1280661 A | 1/2001 |
| CN | 201029436 Y | 3/2008 |
| CN | 201238610 Y | 5/2009 |
| CN | 101518361 A | 9/2009 |
| CN | 101557728 | 10/2009 |
| CN | 100566769 C | 12/2009 |
| CN | 201379072 Y | 1/2010 |
| CN | 201393548 Y | 2/2010 |
| CN | 201821914 U | 5/2011 |
| CN | 201830899 U | 5/2011 |
| CN | 102247640 A | 11/2011 |
| CN | 102934843 A | 2/2013 |
| CN | 102970885 | 3/2013 |
| CN | 202890466 U | 4/2013 |
| CN | 203070141 U | 7/2013 |
| CN | 103237468 A | 8/2013 |
| CN | 104049550 | 9/2014 |
| CN | 203841114 U | 9/2014 |
| CN | 203986103 U | 12/2014 |
| CN | 204335831 U | 5/2015 |
| EA | 19736 | 5/2014 |
| EP | 1712178 A2 | 10/2006 |
| EP | 2404515 A1 | 1/2012 |
| EP | 2460423 A1 | 6/2012 |
| EP | 2908675 | 1/2019 |
| ES | 1091555 U | 10/2013 |
| GB | 2468932 A | 9/2010 |
| GB | 2502053 A | 11/2013 |
| GB | 2502055 A | 11/2013 |
| GB | 2502162 A | 11/2013 |
| GB | 2502163 A | 11/2013 |
| GB | 2502164 A | 11/2013 |

(56) References Cited

FOREIGN PATENT DOCUMENTS

| | | |
|---|---|---|
| GB | 2514767 A | 12/2014 |
| JP | H05212100 | 8/1993 |
| JP | H08-511966 | 12/1996 |
| JP | 3392138 | 1/2003 |
| JP | 2006-018057 | 1/2006 |
| JP | 2006-338178 | 12/2006 |
| JP | 3159830 U | 6/2010 |
| KR | 10-0495099 | 11/2005 |
| KR | 20110002227 U | 3/2011 |
| KR | 1020110132290 | 12/2011 |
| KR | 20120093046 A | 8/2012 |
| KR | 101256914 | 4/2013 |
| RU | 72821 U1 | 5/2008 |
| RU | 2336001 C2 | 10/2008 |
| RU | 2336002 C2 | 10/2008 |
| RU | 94815 U1 | 6/2010 |
| RU | 2425608 | 8/2011 |
| RU | 110608 U1 | 11/2011 |
| SE | 9900703 L | 12/1999 |
| TW | 200928407 A | 7/2009 |
| WO | WO9118860 A1 | 12/1991 |
| WO | WO9418860 A1 | 9/1994 |
| WO | WO9501137 A1 | 1/1995 |
| WO | WO98017131 A1 | 4/1998 |
| WO | WO0064517 A1 | 11/2000 |
| WO | WO2013098397 | 12/2001 |
| WO | WO2012/109371 | 8/2002 |
| WO | WO2013060874 A2 | 5/2003 |
| WO | WO 2004/080216 A1 | 9/2004 |
| WO | WO 2004/095955 A1 | 11/2004 |
| WO | WO 2008139411 | 11/2008 |
| WO | WO2008142015 A2 | 11/2008 |
| WO | WO2009045198 | 4/2009 |
| WO | WO2009063814 | 5/2009 |
| WO | WO2009118085 A1 | 10/2009 |
| WO | WO2009146484 | 12/2009 |
| WO | WO2010073122 | 7/2010 |
| WO | WO2010091593 A1 | 8/2010 |
| WO | WO2010118644 A1 | 10/2010 |
| WO | WO2010145805 A1 | 12/2010 |
| WO | WO2011079932 | 7/2011 |
| WO | WO2013060781 | 10/2011 |
| WO | WO2011147699 A1 | 12/2011 |
| WO | WO 2012/048266 | 4/2012 |
| WO | WO2012117376 A1 | 9/2012 |
| WO | WO2013060784 A2 | 5/2013 |
| WO | WO2013098398 | 7/2013 |
| WO | WO2013138384 A2 | 9/2013 |
| WO | WO2013148810 A1 | 10/2013 |
| WO | WO 2014004437 A1 | 1/2014 |
| WO | WO2014004437 A1 | 1/2014 |
| WO | WO2014037794 A2 | 3/2014 |
| WO | WO2014054035 A1 | 4/2014 |
| WO | WO2015138589 A1 | 9/2015 |
| WO | WO2015192084 A1 | 12/2015 |
| WO | WO 2015192084 A1 | 12/2015 |
| WO | WO2016009202 | 1/2016 |
| WO | WO2016198266 | 12/2016 |

OTHER PUBLICATIONS

International Preliminary Report on Patentability, Application No. PCT/GB2016/051729, dated Sep. 20, 2017, 11 pages.
International Search Report and Written Opinion, Application No. PCT/GB2016/051729, dated Aug. 22, 2016, 20 pages.
Japanese Office Action, Application No. 2017-153826, dated Jun. 19, 2018, 3 pages (6 pages with translation).
Korean Office Action, Application No. 20157010072, dated Apr. 27, 2018, 10 pages (19 pages with translation).
Russian Search Report, Application No. 2016147728/12, dated Mar. 27, 2018, 3 pages (6 pages with translation).
Russian Decision to Grant, Application No. 2015114351/12, dated Aug. 24, 2016, 12 pages.
Chinese Office Action, Application No. 201480055728.2, dated Nov. 17, 2017, 8 pages (20 pages with translation).
Japanese Search Report, Application No. 2016-520611, dated Mar. 28, 2017, 18 pages (46 pages with translation).
Japanese Office Action, Application No. 2016-520611, dated May 9, 2017, 6 pages (11 pages with translation).
Korean Office Action, Application No. 10-2016-7009422, dated Jul. 26, 2017, 8 pages (17 pages with translation).
Australian Third Extended Report, Application No. 2014333571, dated May 23, 2017, 4 pages.
Australian First Examination Report, Application No. 2013261801, dated Jul. 10, 2015, 2 pages.
Australian First Extended Report, Application No. 2013331849, dated Dec. 1, 2015, 3 pages.
Australian First Extended Report, Application No. 2014333571, dated Nov. 25, 2016, 4 pages.
Australian Second Examination Report, Application No. 2013261801, dated Jun. 23, 2016, 3 pages.
Australian Second Extended Report, Application No. 2013331849, dated May 2, 2016, 3 pages.
Australian Second Extended Report, Application No. 2014333571, dated Jan. 23, 2017, 4 pages.
Canadian Office Action, Application No. 2,872,764, dated Aug. 31, 2016, 6 pages.
Canadian Office Action, Application No. 2,872,764, dated Oct. 5, 2015, 6 pages.
Canadian Office Action, Application No. 2,886,922, dated Mar. 4, 2016, 3 pages.
Canadian Office Action, Application No. 2,922,280, dated Jan. 20, 2017, 4 pages.
Chinese Office Action, Application No. 201380025370.4, dated Oct. 11, 2016, 3 pages (8 pages with translation).
Chinese Office Action, Application No. 201380054442.8, dated Jun. 28, 2017, 8 pages.
Corrected IPRP, International Application No. PCT/EP2013/071070, dated Jun. 19, 2015, 13 pages.
EP Office Action, Application No. 13779773, dated Aug. 7, 2017, 2 pages.
European Extended Report, Application No. 13779773.4, dated Jun. 20, 2016, 2 pages.
Japanese Decision to Grant, Application No. 2015-537196, dated Jul. 6, 2017, 3 pages (6 pages with translation).
Japanese Office Action, Application No. 2015-537196, dated Mar. 22, 2016, 3 pages (7 pages with translation).
Japanese Office Action, Application No. 2015-537196, dated Nov. 22, 2016, 4 pages (9 pages with translation).
IPRP for International Patent Application No. PCT/EP2013/071070 dated Nov. 21, 2014.
First Office Action for Chinese Application No. 201380054442.8 dated Aug. 30, 2016.
Notice to File a Response for Korean Application No. 10-2015-7010072 dated Oct. 19, 2016.
Japanese Notice of Allowance for Japanese Application No. 2015-512037 dated Dec. 12, 2015.
Decision to Grant for Russian Application No. 2014150496 dated Feb. 16, 2016.
Japanese Search Report, Application No. 2016-520611, Search completed Mar. 28, 2017, 18 pages (35 pages with translation).
Korean Office Action, Application No. 10-2014-7035201, dated Sep. 23, 2016, 6 pages.
New Zealand Extended Report, Application No. 71778, dated Aug. 15, 2016, 3 pages.
New Zealand First Examination Report, Application No. 717778, dated May 2, 2016, 4 pages.
New Zealand Extended Report, Application No. 717778, dated Nov. 16, 2016, 1 page.
PCT International Preliminary Report on Patentability for PCT/GB2014/053027, dated Dec. 10, 2015, 19 pages.
Application and File History for U.S. Appl. No. 15/231,359, filed Aug. 8, 2016, Inventor: Christopher Lord.
Japanese Office Action, Application No. 2018-033546, dated Feb. 15, 2019, 7 pages (12 pages with translation).

(56) References Cited

OTHER PUBLICATIONS

Canadian Office Action, Application No. 2,997,062, dated Mar. 4, 2019, 6 pages.
Great Britain Search Report, Application No. GB1511566.0, dated Nov. 30, 2015, 4 pages.
Application and File History for U.S. Appl. No. 14/401,511, filed Nov. 14, 2014. Inventors: Lord.
Application and File History for U.S. Appl. No. 15/027,344, filed Apr. 5, 2016. Inventors: Lord et al.
Load Detecting Power Supply. National Semiconductor RD-166 Product Applications Design Center. Dec. 2008, 17 pages.
Sadaphal et al., "Random and Periodic Sleep Schedules for Target Detection in Sensor Networks," Tata Research Development and Design Centre and Department of Computer Science and Engineering— Indian Institute of Technology, Mar. 17, 2008.
International Preliminary Report on Patentability, for PCT/EP2013/059954, dated Jul. 10, 2014.
Written Opinion, for PCT/EP2013/059954, dated Apr. 16, 2014, 5 pages.
International Search Report, for PCT/EP2013/059954, dated Sep. 25, 2013, 8 pages.
Korean Office Action, Application No. KR 10-2014-7035205, dated Aug. 11, 2016, 6 pages.
Chinese Office Action, Application No. CN 201380025370.4, dated Mar. 21, 2016, 9 pages.
International Search Report, for PCT/EP2013/071070, dated Apr. 2, 2014, 6 pages.
Search Report and Written Opinion, for PCT/GB2014/053027, dated Apr. 22, 2015, 13 pages.
Russian Decision to Grant, Application No. 2017145807, dated Oct. 30, 2018, 13 pages.
Korean Office Action, Application No. 10-2018-7038106, dated Oct. 17, 2019, 17 pages.
Chinese Office Action and Search Report, Application No. 201680038584.9, dated Sep. 29, 2019, 17 pages.
European Examination Report, Application No. 18207065.6, dated Feb. 3, 2020, 5 pages.
Terry Ortman: "ProVari Menu Tour", Youtube, Mar. 9, 2011 (Mar. 9, 2011), p. 1 pp., XP054980173, Retrieved from the Internet:, URL:https://www.youtube.com/watch?v=IPKQOgQ42z8, [retrieved on Jan. 28, 2020], (with machine-generated transcript).
European Patent Office Communication, Application No. 16729349.7, dated Feb. 12, 2020, 53 pages.
Dictionary definition for 'Tap', Cambridge dictionary online, accessed Jan. 27, 2020, 1 page.
Notice of Opposition , Application No. EP 13779773.4, dated Oct. 8, 2019, 7 pages.
ProVari Owner's Manual published by ProVape Copyright marking: 2010 ;available on web.archive.org (Dec. 16, 2011).
YouTube "Vlog" "Tips & Tutorial for Using Your ProVape Electronic Cigarette" by Phil Busardo published on Jun. 30, 2012.
Screen capture of ProVari V2 information page on. the ProVape website as it appeared on May 8, 2012 via a query on web.archive.org.
YouTube video "A PBusardo Review—The Provari V2—Provape" published on Feb. 28, 2012.

\* cited by examiner

ELECTRONIC AEROSOL PROVISION SYSTEM WITH MULTIPLE MODES BASED ON SENSED EVENTS

CROSS REFERENCE TO RELATED APPLICATION

The present application is a National Phase entry of PCT Application No. PCT/GB2016/051729, filed Jun. 10, 2016, which claims priority from GB Patent Application No. 1511566.0, filed Jul. 1, 2015, each of which is hereby fully incorporated herein by reference.

FIELD

The present disclosure relates to electronic aerosol provision systems such as nicotine delivery systems (e.g. electronic cigarettes and the like).

BACKGROUND

Electronic aerosol provision systems such as electronic cigarettes (e-cigarettes) generally contain a reservoir of a source liquid containing a formulation, typically including nicotine, from which an aerosol is generated, e.g. through heat vaporization. An aerosol source for an aerosol provision system may thus comprise a heater having a heating element arranged to receive source liquid from the reservoir, for example through wicking/capillary action. While a user inhales on the device, electrical power is supplied to the heating element to vaporize source liquid in the vicinity of the heating element to generate an aerosol for inhalation by the user. Such devices are usually provided with one or more air inlet holes located away from a mouthpiece end of the system. When a user sucks on a mouthpiece connected to the mouthpiece end of the system, air is drawn in through the inlet holes and past the aerosol source. There is a flow path connecting between the aerosol source and an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

Electronic cigarettes will include a mechanism for activating the heater to vaporize the source liquid during use. One approach is to provide a manual activation mechanism, such as a button, which the user presses to activate the heater. In such devices, the heater may be activated (i.e. supplied with electrical power) while the user is pressing the button, and deactivated when the user releases the button. Another approach is to provide an automatic activation mechanism, such as a pressure sensor arranged to detect when a user is drawing air through the device by inhaling on the mouthpiece. In such devices, the heater may be activated when it is detected the user is inhaling through the device and deactivated when it is detected the user has stopped inhaling through the device.

One consideration is for electronic cigarettes to seek to avoid accidental or unintended activation of the heater, which could happen for a number of reasons. For example, with an activation mechanism based on a button, there is a risk the button will be pressed accidentally while the device is in a user's pocket. As another example, with an activation mechanism based on a pressure sensor, there is a risk of ambient pressure changes activating the heater, for example when entering or exiting a tunnel when travelling, or when changing altitude (e.g. on a plane). There is also a potential risk of the heater (and hence vapor generation) being activated by someone who is not an intended user but who picks up the e-cigarette and simply mimics the action of inhalation.

Accidental/unintended heater activation can be undesirable for a number of reasons, for example it can waste battery power, and in more serious cases may result in damage to the electronic cigarette and/or injury to a user, or allow the supply of vapor to an unintended user.

Various approaches are described which seek to help address some of these issues.

SUMMARY

In accordance with some embodiments described herein, there is provided an aerosol delivery device comprising: control circuitry for controlling an operating mode of the device; a motion sensor arranged to detect motion of the device and to output corresponding motion detection signals to the control circuitry; and an airflow sensor arranged to detect a flow of air in the device and to output corresponding airflow detection signals to the control circuitry; wherein the control circuitry is configured to determine from the motion detection signals when there is a tapping event corresponding to the device being tapped by a user and to determine from the airflow detection signals when there is an airflow event corresponding a flow of air in the device, and wherein the control circuitry is configured to control the device to switch from a first operating mode to a second operating mode in response to the detection of a predefined sequence of events comprising at least one tapping event and at least one airflow event.

In accordance with some embodiments described herein, there is provided a method of operating an aerosol delivery device to control an operating mode comprising: detecting, using a motion sensor arranged to detect motion of the device and to output corresponding motion detection signals to the control circuitry and an airflow sensor arranged to detect a flow of air in the device and to output corresponding airflow detection signals to the control circuitry, when there is a predefined sequence of events comprising at least one tapping event and at least one airflow event, and in response thereto, switching the device from a first operating mode to a second operating mode.

In accordance with some embodiments described herein, there is provided an aerosol delivery device comprising: control means for controlling an operating mode of the device; motion sensor means for detecting motion of the device and for outputting corresponding motion detection signals to the control means; and airflow sensor means for detecting a flow of air in the device and for outputting corresponding airflow detection signals to the control means; wherein the control means is configured to determine from the motion detection signals when there is a tapping event corresponding to the device being tapped by a user and to determine from the airflow detection signals when there is an airflow event corresponding a flow of air in the device, and wherein the control means is configured to control the device to switch from a first operating mode to a second operating mode in response to the detection of a predefined sequence of events comprising at least one tapping event and at least one airflow event, for example within a predetermined period of time.

In accordance with some embodiments described herein, there is provided an aerosol delivery device comprising: a control element for controlling the operation of the device; a motion sensor for detecting when a user taps the device and outputting a motion detection signal to the control element in response thereto; and an airflow sensor for detecting when a user inhales or blows through the device and outputting an airflow detection signal to the control element in response thereto, wherein the control element is configured to control an operating characteristic of the device in response to a predefined sequence of detection signals comprising at least one motion detection signal and at least one airflow detection signal being received by the control element, for example within a predetermined period of time.

The approaches described herein are not restricted to specific embodiments such as set out below, but include and contemplate any appropriate combinations of features presented herein. For example, an electronic aerosol provision system may be provided in accordance with the approach described herein which includes any one or more of the various features described below as appropriate.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision system, such as an e-cigarette. Throughout the following description the term "e-cigarette" is sometimes used but this term may be used interchangeably with aerosol (vapor) provision system.

Figure 1:
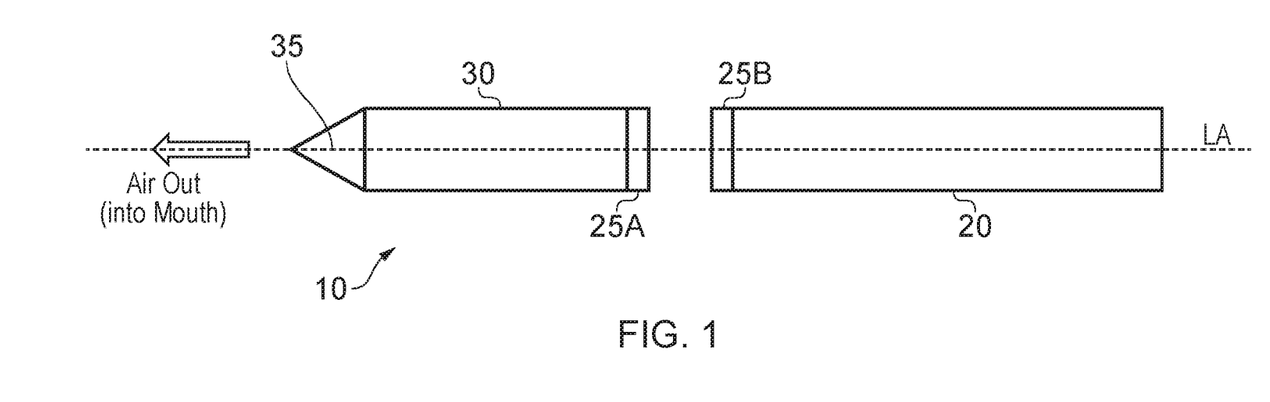
FIG. 1 is a schematic (exploded) diagram of an electronic aerosol provision system such as an e-cigarette in accordance with some embodiments.

FIG. 1 is a schematic diagram of an aerosol/vapor provision system in the form of an e-cigarette 10 in accordance with some embodiments (not to scale). Certain embodiments of the disclosure are described herein in connection with some example e-cigarette configurations (e.g. in terms of the devices' overall appearance and general operating characteristics, e.g. the underlying vapor generation technology). However, it will be appreciated that the same principles can equally be applied for aerosol delivery system having different overall configurations (e.g. having different overall appearance, structure and/or vapor generation technology).

The e-cigarette 10 in this example has a generally cylindrical shape, extending along a longitudinal axis indicated by dashed line LA, and comprising two main components, namely a body 20 and a cartomizer 30. The cartomizer 30 includes an internal chamber containing a reservoir of a source liquid comprising a liquid formulation from which an aerosol is to be generated, a heating element, and a liquid transport element (in this example a wicking element) for transporting source liquid to the vicinity of the heating element. In some example implementations the heating element may itself provide the liquid transport function. The heating element and the element providing the liquid transport function may sometimes be collectively referred to as an aerosol generator/aerosol source/aerosol forming member/vaporizer/atomizer/distiller. The cartomizer 30 further includes a mouthpiece 35 having an opening through which a user may inhale the aerosol from the aerosol generator. The source liquid may be of a conventional kind used in e-cigarettes, for example comprising 0 to 5% nicotine dissolved in a solvent comprising glycerol, water, and/or propylene glycol. The source liquid may also comprise flavorings. The reservoir for the source liquid may comprise a porous matrix or any other structure within a housing for retaining the source liquid until such time that it is required to be delivered to the aerosol generator/vaporizer. In some examples the reservoir may comprise a housing defining a chamber containing free liquid (i.e. there may not be a porous matrix).

As discussed further below, the body 20 includes a re-chargeable cell or battery to provide power for the e-cigarette 10 and a circuit board including control circuitry for generally controlling the e-cigarette 10. The circuit board also includes a motion sensor (e.g. an accelerometer) for detecting motion of the electronic cigarette 10 and outputting corresponding motion detection signals to the control circuitry. It will be appreciated the motion sensor need not necessarily be mounted on the circuit board but could equally be mounted elsewhere in the electronic cigarette 10 with appropriate wiring for communicating motion detection signals to the control circuitry.

In active use, i.e. when the heating element receives power from the battery, as controlled by the control circuitry, the heating element vaporizes source liquid in the vicinity of the heating element to generate an aerosol. The aerosol is inhaled by a user through the opening in the mouthpiece 35. During user inhalation the aerosol is carried from the aerosol source to the mouthpiece opening along an air channel that connects between them.

In this particular example, the body 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector on the body 20 that is used to connect to the cartomizer 30 also serves as a socket for connecting a charging device (not shown) when the body 20 is detached from the cartomizer 30. The other end of the charging device can be plugged into an external power supply, for example a USB socket, to charge or to re-charge the cell/battery in the body 20 of the e-cigarette 10. In other implementations, a cable may be provided for direct connection between the electrical connector on the body 20 and the external power supply and/or the device may be provided with a separate charging port, for example a port conforming to one of the USB formats.

The e-cigarette 10 is provided with one or more holes (not shown in FIG. 1) for air inlet. These holes connect to an air running passage (airflow path) through the e-cigarette 10 to the mouthpiece 35. The air passage includes a region around the aerosol source and a section comprising an air channel connecting from the aerosol source to the opening in the mouthpiece 35.

When a user inhales through the mouthpiece 35, air is drawn into this air passage through the one or more air inlet holes, which are suitably located on the outside of the e-cigarette 10. This airflow (or the resulting change in pressure) is detected by an airflow sensor 215, in this case a pressure sensor, for detecting airflow in electronic cigarette 10 and outputting corresponding airflow detection signals to the control circuitry. The airflow sensor 215 may operate in accordance with conventional techniques in terms of how it is arranged within the electronic cigarette 10 to generate airflow detection signals indicating when there is a flow of air through the electronic cigarette 10 (e.g. when a user inhales or blows on the mouthpiece 35).

When a user inhales (sucks/puffs) on the mouthpiece 35 in use, the airflow passes through the air passage (airflow path) through the electronic cigarette 10 and combines/mixes with the vapor in the region around the aerosol source to generate the aerosol. The resulting combination of airflow and vapor continues along the airflow path connecting from the aerosol source to the mouthpiece 35 for inhalation by a user. The cartomizer 30 may be detached from the body 20 and disposed of when the supply of source liquid is exhausted (and replaced with another cartomizer if so desired). Alternatively, the cartomizer 30 may be refillable.

Generally, the construction and operation of the e-cigarette 10 may follow established techniques in the field of aerosol provision systems except where modified to provide functionality in accordance with the methods and apparatus described herein. It will therefore be appreciated the e-cigarette 10 shown in FIG. 1 is presented as one example implementation of an aerosol provision system according to the present disclosure, and various other implementations can be adopted in the context of other configurations of aerosol provision system. For example, in some embodiments, the cartomizer 30 may be provided as two separable components, namely a cartridge comprising the source liquid reservoir and mouthpiece (which can be replaced when the source liquid from the reservoir is exhausted), and a vaporizer/aerosol generator comprising a heating element (which is generally retained). As another example, the charging facility and/or the heating element itself may connect to an additional or alternative power source, such as a car cigarette lighter socket. More generally, it will be appreciated that embodiments of the disclosure described herein may be implemented in conjunction with any design of electronic aerosol provision system that is based on vaporizing/aerosolizing a source liquid and the underlying operating principles and structural design of other aspects of the aerosol provision system are not significant to the principles of operation in accordance with the embodiments described herein.

Figure 2:
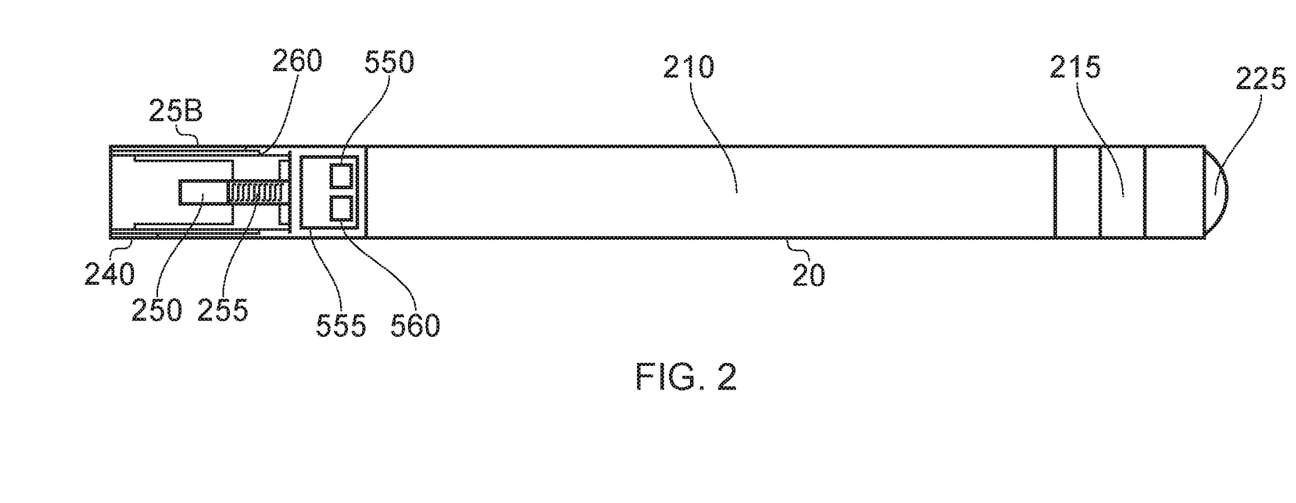
FIG. 2 is a schematic diagram of a main body portion of the e-cigarette of FIG. 1 in accordance with some embodiments.

FIG. 2 is a schematic diagram of the body 20 of the e-cigarette 10 of FIG. 1. FIG. 2 can generally be regarded as a cross-section in a plane through the longitudinal axis LA of the e-cigarette 10. Note that various components and details of the body 20, e.g. such as wiring and more complex shaping, have been omitted from FIG. 2 for reasons of clarity.

As shown in FIG. 2, the body 20 includes a battery or cell 210 for powering the e-cigarette 10, as well as the circuit board 555 comprising the control circuitry 550 and motion sensor 560. In this example the control circuitry 550 is in the form of a chip, such as an application specific integrated circuit (ASIC) or microcontroller, for controlling the e-cigarette 10. The circuit board 555 comprising the control circuitry 550 may be arranged alongside or at one end of the battery 210. The control circuitry 550 may be provided as a single element or a number of discrete elements.

The motion sensor 560 in this example is a conventional solid-state accelerometer, for example a three-axis MEMS accelerometer of the kind frequently used in handheld electronic devices, such as smart phones and games console controllers. The motion sensor 560 may operate in accordance with conventional techniques in terms of how it is arranged to generate motion detection signals indicating when the device undergoes acceleration. More generally, the motion sensor 560 may comprise any form of motion detecting technology for detecting motion of an object. It will furthermore be appreciated the term acceleration is used herein to encompasses both acceleration and deceleration, that is to say, the acceleration may be positive or negative along any given direction.

The control circuitry 550 is connected to the pressure sensor 215 to detect an inhalation on mouthpiece 35 and, as mentioned above, this aspect of detecting when there is an airflow in the electronic cigarette 10 and generating corresponding airflow detection signals may be conventional.

In addition to being configured to support the conventional operating aspects of the e-cigarette 10 in accordance with generally established techniques, the control circuitry 550 is further configured in accordance with embodiments of the disclosure as described herein to control an operating mode of the e-cigarette 10, and in particular to control when the e-cigarette 10 switches between different operating (use) modes, based on signals received from the motion sensor 560 and or the airflow sensor 215, as discussed further below.

The body 20 further includes a cap 225 to seal and protect the far (distal) end of the e-cigarette 10. There is an air inlet hole provided in or adjacent to the cap 225 to allow air to enter the body and flow past the sensor unit 215 when a user inhales on the mouthpiece 35.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A, thereby helping to ensure good electrical connectivity between the body 20 and the cartomizer 30. The body connector 240 and the electrical contact 250 are separated by a spacer 260, which is made of a non-conductor (such as plastic) to provide good insulation between the two electrical terminals. The spacer 260 is shaped to assist with the mutual mechanical engagement of connectors 25A and 25B.

Figure 3:
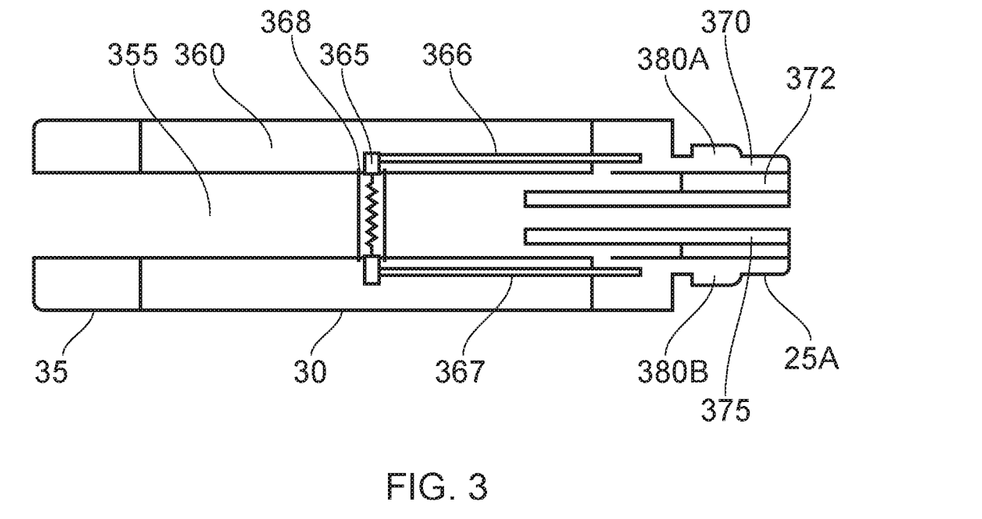
FIG. 3 is a schematic diagram of an aerosol source portion of the e-cigarette of FIG. 1 in accordance with some embodiments.

FIG. 3 is a schematic diagram of the cartomizer 30 of the e-cigarette 10 of FIG. 1 in accordance with some embodiments. FIG. 3 can generally be regarded as a cross-section in a plane through the longitudinal axis LA of the e-cigarette 10. Note that as with the other figures, various components and details of the device, e.g. such as wiring and more complex shaping, have been omitted for reasons of clarity.

The cartomizer 30 includes an aerosol source 365, 368 arranged in an air passage 355 extending along the central (longitudinal) axis of the cartomizer 30 from the mouthpiece 35 to the connector 25A for joining the cartomizer to the body 20. The aerosol source comprises a resistive heating element 365 adjacent a wicking element (liquid transport element) 368 which is arranged to transport source liquid from a reservoir of source liquid 360 to the vicinity of the heating element 365 for heating.

The reservoir of source liquid 360 in this example is provided around the air passage 335 and may be implemented, for example, by providing cotton or foam soaked in source liquid. Ends of the wicking element 365 are in contact with the source liquid in the reservoir 360 so that the liquid is drawn along the wicking element to locations adjacent the extent of the heating element 365.

The general configuration of the wicking element 368 and the heating element 365 may follow conventional techniques. For example, in some implementations the wicking element 368 and the heating element 365 may comprise separate elements, e.g. a metal heating wire wound around/wrapped over a cylindrical wick, the wick, for instance, consisting of a bundle, thread or yarn of glass fibers. In other implementations, the functionality of the wicking element 368 and the heating element 365 may be provided by a single element. That is to say, the heating element 365 itself may provide the wicking function. Thus, in various example implementations, the heating element/wicking element may comprise one or more of: a metal composite structure, such as porous sintered metal fiber media (Bekipor® ST) from Bakaert, a metal foam structure, e.g. of the kind available from Mitsubishi Materials; a multi-layer sintered metal wire mesh, or a folded single-layer metal wire mesh, such as from Bopp; a metal braid; or glass-fiber or carbon-fiber tissue entwined with metal wires. The "metal" may be any metallic material having an appropriate electric resistivity to be used in connection/combination with a battery. The resultant electric resistance of the heating element will typically be in the range 0.5-5 Ohm. Values below 0.5 Ohm could be used but could potentially overstress the battery. The "metal" could, for example, be a NiCr alloy (e.g. NiCr8020) or a FeCrAl alloy (e.g. "Kanthal") or stainless steel (e.g. AISI 304 or AISI 316).

The heating element 365 is powered through lines 366 and 367, which are in turn connectable to opposing polarities (positive and negative, or vice versa) of the battery 210 via connector 25A and under the control of the control circuitry 355 (the details of the wiring between the power lines 366 and 367 and connector 25A are omitted from FIG. 3 for simplicity of representation).

The connector 25A includes an inner electrode 375, which may be silver-plated or made of some other suitable metal. When the cartomizer 30 is connected to the body 20, the inner electrode 375 contacts the electrical contact 250 of the body 20 to provide a first electrical path between the cartomizer 30 and the body 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring is surrounded by the cartomizer connector 370, which may be silver-plated or made of some other suitable metal or conducting material. When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body 20 to the heating element 365 in the cartomizer 30 via supply lines 366 and 367 under the control of the control circuitry 550.

The cartomizer connector 370 is provided with two lugs or tabs 380A, 380B, which extend in opposite directions away from the longitudinal axis of the e-cigarette 10. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer 30 and body 20 are held in a fixed position relative to one another, without wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
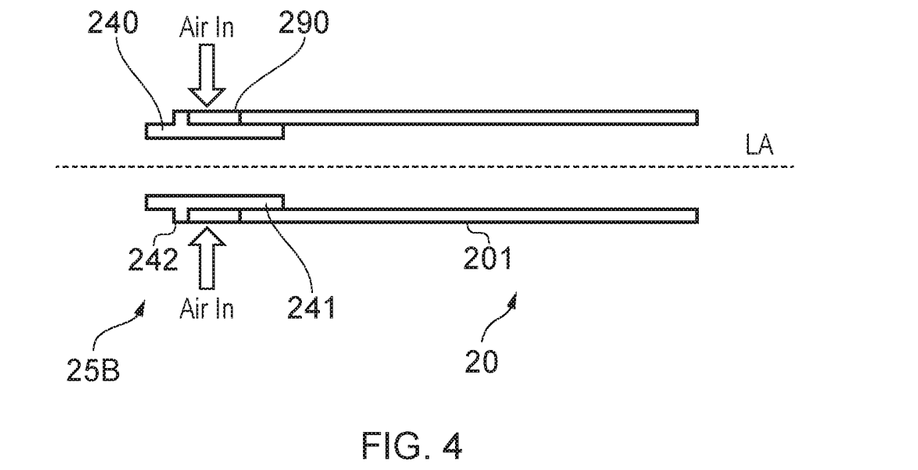
FIG. 4 is a schematic diagram showing certain aspects of one end of the main body portion of the e-cigarette of FIG. 1 in accordance with some embodiments.

FIG. 4 is a schematic diagram of certain details of the connector 25B at the end of the body 20 in accordance with some embodiments (but omitting for clarity most of the internal structure of the connector as shown in FIG. 2, such as spacer 260). In particular, FIG. 4 shows the external housing 201 of the body 20, which generally has the form of a cylindrical tube. This external housing 201 may comprise, for example, an inner tube of metal with an outer covering of paper or similar.

The body connector 240 extends from this external housing 201 of the body 20. The body connector 240 as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette 10. Surrounding the shaft portion 241 of the body connector 240, where the shaft portion 241 does not overlap with the external housing 201, is a collar or sleeve 290, which is again in a shape of a cylindrical tube. The collar 290 is retained between the lip portion 242 of the body connector 240 and the external housing 201 of the body 20, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow past sensor 215 when a user inhales on the mouthpiece 35. However, for this particular example aerosol provision system, the majority of air that enters the device when a user inhales flows through collar 290 and body connector 240 as indicated by the two arrows in FIG. 4.

As noted above, some example aerosol delivery devices in accordance with some embodiments of the present disclosure seek to help address or reduce some of the issues associated with accidental/unintended activation of an aerosol delivery device. This is done in some example implementations by the control circuitry controlling when an aerosol delivery device switches between different operating modes (use modes) based on signaling received from a motion sensor (e.g. an accelerometer) and an airflow sensor (e.g. a pressure sensor).

The electronic cigarette 10 represented in FIGS. 1 to 4 can operate in a number of different modes. In one operating mode, which may be referred to as an active mode or vapor generation mode, the control circuitry 550 is configured to cause power to be supplied from the battery 210 to the heating element 365 (e.g. by driving an appropriately configured transistor switch) to cause liquid in the vicinity of the heating element to be vaporized for inhalation by a user. In another operating mode, which may be referred to as a standby mode or ready mode, the control circuitry 550 may be configured to cut the supply of power to the heating element 365 so that no vapor is generated, but to automatically switch to the active mode (and hence supply power to the heating element 365) when it is determined that a user is inhaling on the mouthpiece 35 of the electronic cigarette 10 based on information/signaling received from the pressure sensor 215. In another mode, which may be referred to as a safe mode or an off mode, the control circuitry 550 is configured to prevent the supply of power to the heating element 365 so that no vapor is generated, but unlike the standby mode, in the safe mode the control circuitry 550 is not configured to automatically switch to the active mode simply in response to a user inhaling on the device. Rather, in the safe mode the control circuitry 550 is configured to switch to the active mode in response to a predefined combination of signals being received from the accelerometer 560 and the pressure sensor 215, for example, within a predefined period of time.

Thus, in accordance with certain example implementations in accordance with some embodiments of the disclosure, the control circuitry 550 is configured to (1) determine from motion detection signals received from the accelerometer 560 when there is a tapping event corresponding to the electronic cigarette 10 being tapped by a user, and (2) to determine from airflow detection signals received from the airflow sensor 215 when there is an airflow event corresponding to a flow of air being detected in the device (e.g. because a user inhales on the mouthpiece 35). The control circuitry 550 is furthermore configured to control the device to switch from the safe (off) mode to the active (in use) mode in response to the detection of a predefined sequence of events comprising at least one tapping event and at least one airflow event within a predefined period of time. In one particular example the predefined sequence of events may comprise two tapping events followed by an airflow event and the predefined period of time may be three seconds. Thus, to switch the electronic cigarette from the safe mode to the active mode, a user taps the device twice and begins inhaling within a three second period. This switches the device to the active mode in which power is supplied to the heating element, so that as the user continues to inhale on the device, vapor generated by the heating element 365 may be inhaled. It will of course be appreciated the predefined period of time can be different in different implementations. For example, in some cases the predefined period of time could be five seconds, rather than three seconds.

A tapping event may, for example, correspond with a user tapping the electronic cigarette 10 on a surface, or tapping the device with his or her finger. Such a tap will generate a relatively brief acceleration of the electronic cigarette 10 which is reflected in the motion detection signals from the accelerometer 560. Thus, the control circuitry 550 may be configured to process the motion detection signals received from the accelerometer 560 to determine when there has been a tapping event by identifying when the motion detection signals indicate the occurrence of an acceleration of the electronic cigarette 10 which is greater than a threshold acceleration amount. An appropriate threshold acceleration amount for a given configuration of electronic cigarette 10 may, for example, be determined empirically during a design phase of that particular electronic cigarette 10. Appropriate values to use will depend on a number of factors, for example the intended activation force to give rise to a tap detection and the mass of the device. For example, in one implementation, it may be determined that a tapping event has occurred if the control circuitry 550 determines the electronic cigarette 10 has undergone an acceleration of greater than around 5 m/s$^2$ (0.5 g) for less than 50 ms (0.05 s).

An airflow event may, for example, correspond with a user inhaling on the electronic cigarette 10. This will generate an airflow in the device which is reflected in the airflow detection signals from the pressure sensor 215 in accordance with conventional techniques. Thus, the control circuitry 550 may be configured to process the signals received from the pressure sensor 215 to determine when there is an airflow event by identifying when the airflow detection signals indicate there is a change in pressure in the airflow path of the device which is more than a threshold pressure change amount. The pressure change may, for example, be measured by comparing a current pressure measurement with a running average of pressure measurements over a preceding period, for example over 1, 2, 3, 4, 5, or 10 seconds. In another implementation the control circuitry 550 may be configured to process the signals received from the pressure sensor 215 to determine when there is an airflow event by identifying when the airflow detection signals indicate a pressure in the airflow path of the device has passed (e.g. fallen below) a threshold pressure level. In any event, an appropriate threshold level may again be determined empirically during a design phase of the particular electronic cigarette 10. Appropriate values to use will depend on a number of factors, for example the intended inhalation effort and corresponding air flow rate intended to give rise to an airflow detection event, as well as how the pressure sensor 215 is coupled to the device's flow path (which will determine the pressure drop at the sensor for a given inhalation effort). In one particular example implementation, the control circuitry 550 may be configured to determine an airflow event has started if the pressure sensor indicates a change (e.g. a drop) in pressure measured relative to a previous pressure measurement (or average of a number of previous pressure measurements) that is greater than 30 Pascals.

When the device is in the active mode, the control circuitry 550 monitors for when the user is deemed to have stopped inhaling on the device. When the control circuitry 550 determines the user has stopped inhaling on the device, the control circuitry 550 controls the device to switch from the active mode to the standby mode. The determination of when the user has stopped inhaling on the device may be based on signaling received from the pressure sensor 215 in accordance with conventional techniques. Thus, the control circuitry 550 may, when in the active mode, be configured to process the signals received from the pressure sensor 215 to determine when there is an airflow reduction event by identifying when the airflow detection signals indicate there is a change in pressure that is more than a threshold pressure change amount. In this regard, the process of detecting an airflow reduction event (when a user stops inhaling on the device) may follow the same general principles as the process for detecting an airflow event (when a user begins inhaling on the device), except the pressure change will be in a different direction. Thus, an airflow reduction event may be deemed to occur when the pressure sensor signals indicate at least a threshold pressure change relative to a running average of pressure measurements over a preceding period, for example over 0.5, 1 or 2 seconds. In another implementation the control circuitry may be configured to process the signals received from the pressure sensor to determine when there is an airflow reduction event by identifying when the airflow detection signals indicate a pressure in the airflow path of the device has passed (e.g. risen above) a threshold pressure level. In any event, an appropriate threshold level for identifying an airflow reduction event may again be determined empirically during a design phase of the particular electronic cigarette 10. Appropriate values to use will again depend on a number of factors, for example the magnitude of the drop in air flow rate intended to give rise to an airflow reduction event, as well as how the pressure sensor 215 is coupled to the device's flow path. In one particular example implementation, the control circuitry 550 may be configured to identify an airflow reduction event has occurred if the pressure sensor 215 indicates a change (e.g. an increase) in pressure measured relative to a previous pressure measurement (or average of a number of previous pressure measurements) that is greater than 30 Pascals.

When the device is in the standby mode the control circuitry 550 is configured to monitor for an airflow event correspond with a user inhaling on the electronic cigarette 10 and to switch back into active mode if this is detected. That is to say, the process of switching from standby mode to active mode is different from the process of switching from safe mode to active mode. In particular, switching from safe mode to active mode is based on detecting a predefined sequence of at least one tapping event (acceleration event) and at least one airflow event (inhalation event) within a predefined period of time, whereas switching from standby mode to active mode is based simply on detecting an airflow event (inhalation event).

When the device is in standby mode, in addition to monitoring for an airflow event to determine whether to switch back to active mode, the control circuitry 550 also monitors for a further predefined sequence of events, for example comprising a plurality of tapping events, for example two tapping events, occurring within a predefined period of time, for example within one or two seconds. If such a predefined sequence of events is identified, the control circuitry 550 is configured to switch the electronic cigarette 10 from the standby mode back to the safe mode. This provides a user with a convenient way of returning the device to safe mode once a session of use is completed (i.e. after the user has taken a plurality of puffs spread over a number of minutes during which the electronic cigarette 10 automatically switches between active mode and standby mode according to when the user is inhaling on the device). Alternatively, or in addition, the control circuitry 550 may be configured to switch from the standby mode to the safe mode if it is determined the by the control circuitry 550 that the electronic cigarette 10 has remained in standby mode for longer than a predetermined threshold duration of time (that is to say, no airflow events have been detected within the predetermined threshold duration of time). For example, the control circuitry 550 may be configured to switch the electronic cigarette 10 from standby mode to safe mode if the device has remained in standby mode for greater than 5, 10, 15 or 20 minutes, or another period depending on how the device has been configured. This, as with other aspects of the operation (such as the predefined sequence of events for switching from safe mode to active mode), may in some example implementations be user configurable.

Figure 5:
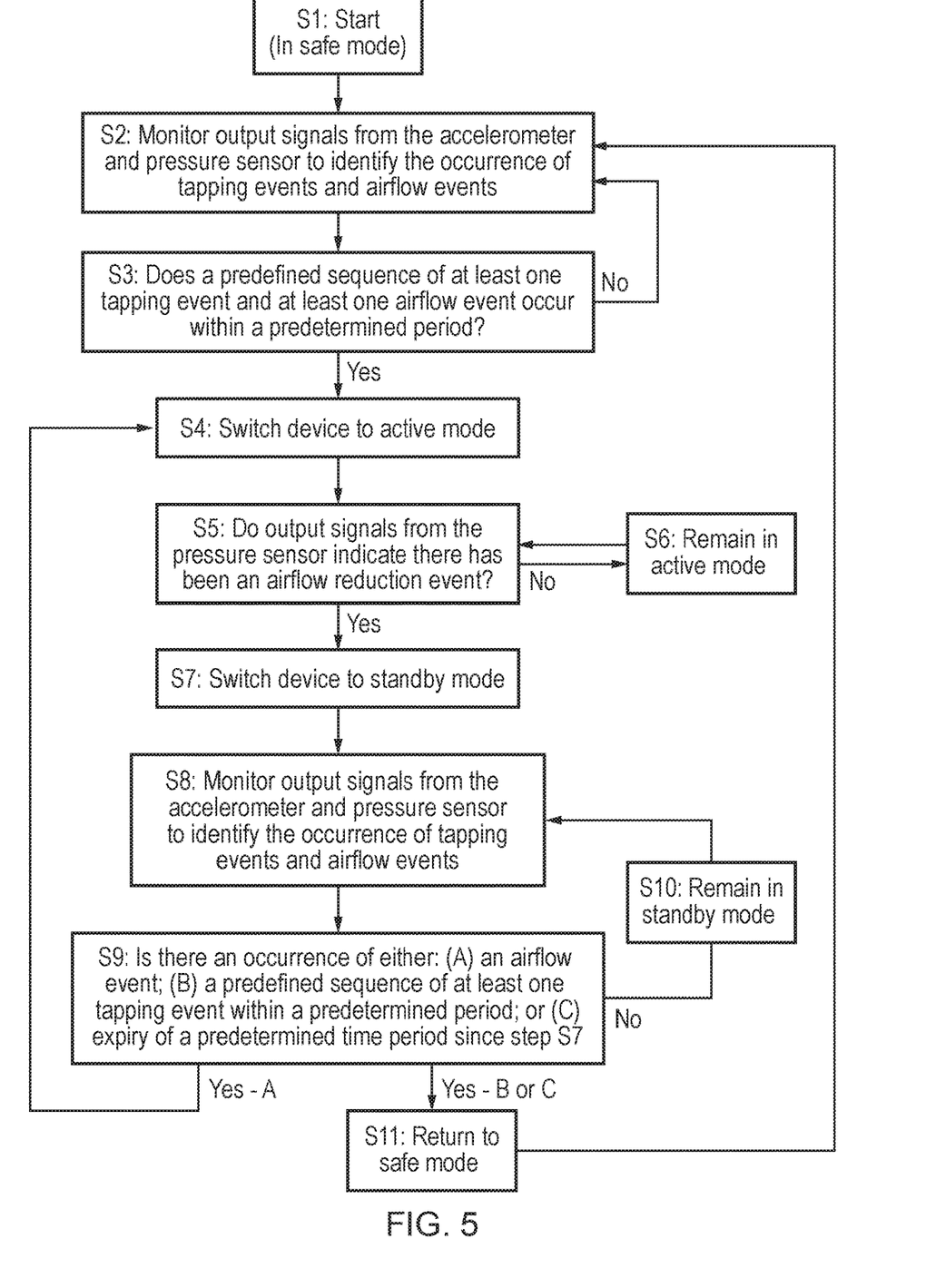
FIG. 5 is a schematic flow diagram representing operation of an electronic aerosol provision system such as an e-cigarette in accordance with some embodiments.

FIG. 5 is a flow diagram schematically representing steps of a method of operating an electronic vapor provision system in accordance with certain embodiments of the disclosure in accordance with the principles described herein. Thus, in the context of the example e-cigarette 10 represented in FIGS. 1 to 4, the control circuitry 550 is configured to provide functionality in accordance with the method represented in FIG. 5.

The processing begins in S1 in which the device is assumed to be in safe mode. This might, for example, be the default operating mode when the body 20 and cartomizer 30 are first connected and/or the control circuitry 550 is first powered up.

In S2, the control circuitry 550 monitors output signals from the accelerometer 560 and pressure sensor 215 to identify when tapping events and airflow events occur as discussed above.

In S3, the control circuitry 550 determines whether or not a predefined sequence of at least one tapping event and at least one airflow event has occurred within a predetermined period. As noted above, in this example implementation the predefined sequence corresponds with two tapping events followed by an airflow event within a 3 second period.

In this case S3 may be implemented in practice by the control circuitry 550 recording when tapping events occur, and then for each airflow event checking whether there have been two tapping events in the preceding 3 seconds. In this particular example it is assumed the predefined sequence comprises two, and only two, tapping events in the relevant period. That is to say, three (or more) tapping events followed by an airflow event within the predefined period would not be considered to correspond with the predefined sequence and would not cause the control circuitry 550 to switch the electronic cigarette 10 from safe mode to active mode. However, in another implementation the occurrence of two tapping events followed by an airflow event within the predefined period may switch the electronic cigarette 10 from safe mode to active mode regardless of whether there were additional tapping or airflow events in the predefined period prior to this sequence occurring. That is to say, three (or more) tapping events followed by an airflow event within a three second period may in some implementations also switch the device from safe mode to active mode. Similarly, an airflow event followed by two tapping events followed by another airflow event may in some implementations switch the device from safe mode to active mode.

In some other examples, S3 may be implemented in practice by the control circuitry 550 identifying when there is an occurrence of the relevant number of tapping events associated with the predefined sequence and then monitoring for an airflow detection event within the predefined time. If an airflow detection event is detected within the relevant period of time, it is determined the predefined sequence of event has occurred, and if an airflow detection event is not detected within the period of time, it is determined the predefined sequence of events for switching the device out of safe mode has not occurred (although as discussed below may be taken as an instruction to switch the device into safe mode it is not already in safe mode). In this sense it will be appreciated the predefined period of time in which the sequence of events is to be detected may be associated with the time from the last tapping event of the sequence to a following airflow detection event, rather than the time in which all the tapping events and airflow events occur. That is to say, the detection of a predefined sequence of events comprising at least one tapping event and at least one airflow event within a predefined period of time should be interpreted as the detection of a predefined sequence of events comprising at least one tapping event and at least one airflow event occurring in association with a predefined period of time.

If it is determined in S3 that the predefined sequence of events has not occurred within the predetermined period of time, processing follows the branch marked "No" from S3 back to S2 in which the control circuitry 550 continues to monitor the output signals from the accelerometer 560 and pressure sensor 215 to identify when tapping events and airflow events occur.

If, on the other hand, it is determined in S3 that the predefined sequence of events has occurred within the predetermined period of time, processing follows the branch marked "Yes" from S3 to S4.

In S4 the control circuitry 550 acts to switch the electronic cigarette 10 from safe mode to active mode. Thus, in this example, the control circuitry 550 causes power to be supplied to the heating element 365 of the electronic cigarette 10 so that vapor is generated and may be inhaled by a user.

Whilst the electronic cigarette 10 remains in active mode, the control circuitry 550 continues to monitor the pressure sensor signals to determine when the user stops inhaling on the electronic cigarette 10 (i.e. when there is an airflow reduction event), as schematically represented in S5.

If it is determined in S5 there has not been an airflow reduction event (i.e. the user is still inhaling on the electronic cigarette 10), the control circuitry 550 maintains the supply of power to the heating element 365 while continuing to monitor for when there is an airflow reduction event, as schematically indicated in FIG. 5 by S6.

If, on the other hand, it is determined in S5 that there has been an airflow reduction event, that is to say it is determined the user has stopped inhaling on the electronic cigarette 10, processing follows the branch marked "Yes" from S5 to S7.

In S7 the control circuitry 550 acts to switch the electronic cigarette 10 from active mode to standby mode, i.e., the control circuitry 550 cuts power to the heating element 365.

In S8, while in the standby mode, the control circuitry 550 monitors output signals from the accelerometer 560 and pressure sensor 215 to identify when tapping events and airflow events occur.

In S9, the control circuitry 550 determines from the monitoring in S8 whether any of the following occurs:

(A) an airflow event is detected (i.e. a user inhales on the electronic cigarette 10);

(B) a predefined sequence comprising at least one tapping event within a predefined period of time is detected. This predefined sequence is different from the predefined sequence for switching the device from safe mode to active mode, for example it may be a sequence of two tapping events within one second;

(c) a predefined period of time passes with the electronic cigarette 10 remaining in standby mode, for example 15 minutes.

If none of these situations occur, the control circuitry 550 is configured to maintain the electronic cigarette 10 in standby mode as schematically indicated in FIG. 5 in S10.

If, on the other hand, it is determined that situation (A) has occurred, i.e. an airflow event is detected while the electronic cigarette is in standby mode, the control circuitry 550 is configured to follow the branch marked "Yes—A" from S9 to return to S4 in which the electronic cigarette 10 returns to active mode (vapor generation mode).

If, on the other hand, it is determined that situation (B) or situation (C) has occurred, i.e. two tapping events are detected within one second or the electronic cigarette 10 remains in standby mode for more than 15 minutes, the control circuitry 550 is configured to cause the electronic cigarette 10 to switch from standby mode back to safe mode by following the branch marked "Yes—B or C" from S9 to S11. Processing may then return to S2 and continue as discussed above.

Accordingly, the processing of S9 allows a user to readily return the electronic cigarette 10 from standby mode to active mode during an ongoing session of use by simply inhaling on the device. Alternatively, the user may manually return the electronic cigarette 10 to safe mode by performing the predefined deactivation sequence within the relevant time (i.e. in this particular example two taps within one second) when the user has finished a session of use. If the user takes no action, for example because the user has finished an ongoing session of use but does not manually return the electronic cigarette 10 to the safe mode, the electronic cigarette 10 automatically returns to safe mode after the predetermined time period spent continuously in standby mode has elapsed (which in this example implementation is 15 minutes).

In some implementations, the predefined sequence of events for switching the device out of safe mode (e.g. in association with S3 in FIG. 5) comprises a given number of tapping events followed by an airflow event within a period of time, and the predefined sequence of events for switching the device back to safe mode (e.g. in association with situation (B) in S9 in FIG. 5) comprises the same given number of tapping events, but without being followed by an airflow event within a period of time (which may or may not be the same as the period of time associated with switching the device out of safe mode).

Thus, in accordance with some of the principles described above, approaches are provided that help reduce a risk of unintended/accidental activation of an aerosol generation operating mode of an aerosol provision system while the devices in a safe mode. This is achieved by relying on the occurrence of a predefined sequence of at least one tapping event and at least one airflow event within a predetermined period to cause the device to switch from the safe mode to the active mode. The device may then automatically switch from the active mode to a standby mode when a user stops inhaling on the device. Furthermore, approaches in accordance with certain embodiments allow for a user to conveniently switch between the active mode and the standby mode during an ongoing session of use by switching between these modes automatically in dependence on whether or not air is being drawn through the device. Furthermore still, once a user has finished a session of use, the user can readily return the device to the safe mode by performing the predefined sequence of at least one tapping event within the corresponding period of time (e.g. two taps in one second in this example). If the device remains in standby mode without use for more than a predetermined period of time, the device may automatically return to safe mode.

In the context of an electronic cigarette, approaches in accordance with the principles described herein may be especially convenient for users since the process of tapping a device before use mimics a common user behavior associated with conventional cigarettes, which users will often tap, for example to help pack loose tobacco in the end of the cigarette, before use.

It will be appreciated various modifications to the apparatus and methods described above may be implemented in accordance with certain embodiments of the disclosure.

For example, it will be appreciated that various different predefined sequences may be defined for causing the device to switch between different operating votes. For example, rather than rely a sequence of two tapping events and an airflow event within three seconds to activate the device (i.e. to switch from safe mode to active mode), different implementations may adopt different activation sequences. Furthermore, in some examples a user may be provided with the ability to select their own preferred activation sequence and/or there may be multiple different activation sequences for switching the device from safe mode to active mode.

It will further be appreciated that in addition to the various example operating modes discussed above (safe mode, active mode and standby mode), a device in accordance with some embodiments may also support other modes of operation.

For example, a device may additionally support what may be referred to as a lock mode. The lock mode may be broadly similar to the safe mode in terms of how the device is configured to prevent the supply of power to the heating element, but unlike the safe mode, in the locked mode the device does not switch to the active mode in response to the predefined sequence of tapping and airflow events that switches the device from safe mode to active mode. Instead, a different process is required to switch the device out of lock mode, for example a more complex sequence of tapping and airflow events that may be user defined, or some other user input, for example entry of a Personal Identification Number (PIN) on a device, such as a smart phone, that is communicatively coupled to the device. Thus the locked mode provides what might be seen as an even deeper level of protection against unintended activation of the heater than the safe mode in having a deactivation mechanism that is more complex.

In the examples described above, it is assumed the accelerometer is a three axis accelerometer and a tapping event may be considered to occur whenever there is a threshold amount of acceleration along any direction. However, in other example implementations the control circuitry may be configured to detect tapping events only in response to acceleration along a given direction, for example along a longitudinal axis of the electronic cigarette. This may be because, for example, the accelerometer is only configured to measure acceleration along this axis, or because the control circuitry is configured to process the outputs from a multi-axis accelerometer to determine the component along this axis. Furthermore, the control circuitry may be configured to process the signals from a multi-axis accelerometer and separately detect tapping events in different directions. For example, the control circuitry be configured to distinguish longitudinal tapping events (acceleration along the longitudinal axis of the device) and sideways tapping events (acceleration perpendicular to the longitudinal axis of the device). In this case the a predefined sequence for switching between operating modes may comprise a combination of tapping events along different directions, for example two longitudinal (end-on) taps followed by one sideways (side-on) tap.

Furthermore, whilst in the examples described above the airflow event has primarily corresponded to a user inhaling on the electronic cigarette, in principle, the airflow event could equally correspond a user blowing on an electronic cigarette. For example, the activation sequence for switching the electronic cigarette from safe mode to active mode might comprise a user tapping the device a number of times and then blowing through the device, before sucking to inhale a generated aerosol.

In some cases the control circuitry may be configured to switch the device from a safe mode to a standby mode, rather than directly to an active mode in response to detecting the predefined sequence of tapping and/or airflow events. In some cases the predefined signals may comprise only tapping events. For example, the control circuitry may be configured to switch the device from a safe mode to a standby mode or to an active mode in response to detecting a predefined sequence of tapping events occurring within a predefined period, with or without an associated airflow event.

It will further be appreciated that the timings presented above are examples in accordance with certain implementations, but may be different, and may furthermore be user configurable, in other implementations. For example, the predefined period of time for the predefined sequence of events for switching from the safe mode (first operating mode) to the active mode (second operating mode) may, instead of being 3 seconds, be a different period of time, for example it may be a period of time in a range selected from the group comprising: 1 second to 1.5 seconds; 1.5 seconds to 2 seconds; 2 seconds to 2.5 seconds; 2.5 seconds to 3 seconds; 3 seconds to 3.5 seconds; 3.5 second to 4 seconds; less than 5 seconds and less than 10 seconds. Similarly, the predetermined period of time after which the device will automatically switch from the standby mode (third operating mode) to the safe mode (first operating mode) may instead of being 15 minutes, be a different time, for example it may be a time in a range selected from the group comprising: 1 minute to 1.5 minutes; 1.5 minutes to 2 minutes; 2 minutes to 2.5 minutes; 2.5 minutes to 3 minutes; 3 minutes to 3.5 minutes; 3.5 minute to 4 minutes; 5 minutes to 10 minutes; and 10 minutes to 20 minutes.

Thus, there has been described an aerosol delivery device comprises control circuitry for controlling an operating mode of the device, a motion sensor arranged to detect motion of the device and to output corresponding motion detection signals to the control circuitry, and an airflow sensor arranged to detect a flow of air in the device and to output corresponding airflow detection signals to the control circuitry. The control circuitry is configured to determine from the motion detection signals when there is a tapping event corresponding to the device being tapped by a user and to determine from the airflow detection signals when there is an airflow event corresponding a flow of air being detected in the device. The control circuitry is further configured to control the device to switch from a first operating mode, such as standby mode, to a second operating mode, such as an active mode, in response to the detection of a predefined sequence of events comprising at least one tapping event and at least one airflow event within a predefined period of time.

While the above described embodiments have in some respects focused on some specific example aerosol provision systems, it will be appreciated the same principles can be applied for aerosol provision systems using other technologies. That is to say, the specific manner in which various aspects of the aerosol provision system which are not directly relevant to establishing whether a fault condition has arisen for a heating element in accordance with the approaches described herein is not significant to the principles underlying certain embodiments. For example, configurations based on the systems disclosed in US 2011/0226236 could be used in other implementations.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An aerosol delivery device comprising:
   control circuitry for controlling an operating mode of the device;
   a motion sensor arranged to detect motion of the device and to output corresponding motion detection signals to the control circuitry; and
   an airflow sensor arranged to detect a flow of air in the device and to output corresponding airflow detection signals to the control circuitry;
   wherein the control circuitry is configured to determine from the motion detection signals when there is a tapping event corresponding to the device being tapped by a user and to determine from the airflow detection signals when there is an airflow event corresponding a flow of air in the device, and wherein the control circuitry is configured to control the device to switch from a first operating mode to a second operating mode in response to the detection of a first predefined sequence of events comprising at least one tapping event and at least one airflow event.

2. The aerosol delivery device of claim 1, wherein the first predefined sequence of events comprises at least one tapping event followed by at least one airflow event.

3. The aerosol delivery device of claim 1, wherein the first predefined sequence of events comprises a plurality of tapping events.

4. The aerosol delivery device of claim 1, wherein the first predefined sequence of events consists of two tapping events followed by one airflow event.

5. The aerosol delivery device of claim 1, wherein the first predefined sequence of events comprises the at least one tapping event and the at least one airflow event occurring in association with a predefined period of time.

6. The aerosol delivery device of claim 5, wherein the predefined period of time is within a range selected from the group consisting of: 1 second to 1.5 seconds; 1.5 seconds to 2 seconds; 2 seconds to 2.5 seconds; 2.5 seconds to 3 seconds; 3 seconds to 3.5 seconds; 3.5 second to 4 seconds; less than 5 seconds; and less than 10 seconds.

7. The aerosol delivery device of claim 1, wherein the device comprises a heating element and wherein the switch from the first operating mode to the second operating mode comprises the control circuitry activating a supply of power to the heating element.

8. The aerosol delivery device of claim 1, wherein the control circuitry is further configured to determine from the airflow detection signals when there is an airflow reduction event corresponding to a reduction in the flow of air in the device when the device is in the second operating mode and, in response thereto, to control the device to switch from the second operating mode to a third operating mode in which the control circuitry is configured to control the device to switch back to the second operating mode in response to the detection of an airflow event.

9. The aerosol delivery device of claim 1, wherein the motion sensor is an accelerometer.

10. The aerosol delivery device of claim 9, wherein the control circuitry is configured to determine a tapping event has occurred when the motion detection signals indicate the device has undergone an acceleration that exceeds a threshold acceleration.

11. The aerosol delivery device of claim 1, wherein the airflow sensor comprises a pressure sensor configured to measure air pressure in an airflow path of the device.

12. The aerosol delivery device of claim 11, wherein the control circuitry is configured to determine an airflow event has occurred when the airflow detection signals indicate there has been a change in pressure in the airflow path of the device that is more than a threshold pressure change or when the airflow detection signals indicate the pressure in the airflow path has crossed a threshold pressure level.

13. The aerosol delivery device of claim 1, wherein the control circuitry is further configured to control the device to switch from the second operating mode to the first operating mode in response to detection of a second predefined sequence of events which is different from the first predefined sequence of events for switching the device from the first operating mode to the second operating mode.

14. The aerosol delivery device of claim 13, wherein the second predefined sequence of events comprises at least one tapping event which is not followed by an airflow event within a defined period of time.

15. The aerosol delivery device of claim 1, wherein the control circuitry is further configured to control the device to switch from the second operating mode to the first operating mode in response to no airflow events being detected within a predetermined period of time.

16. The aerosol delivery device of claim 15, wherein the predetermined period of time is within a range selected from the group consisting of: 1 minute to 1.5 minutes; 1.5 minutes to 2 minutes; 2 minutes to 2.5 minutes; 2.5 minutes to 3 minutes; 3 minutes to 3.5 minutes; 3.5 minute to 4 minutes; 5 minutes to 10 minutes; and 10 minutes to 20 minutes.

17. The aerosol delivery device of claim 15, wherein the control circuitry is configured to adjust the predetermined period of time in response to receiving configuration setting information.

18. The aerosol delivery device of claim 1, further comprising a power supply, a heating element and a reservoir of source liquid, wherein the control circuitry is configured to control a supply of power from the power supply to the heating element to selectively generate an aerosol from source liquid in the vicinity of the heating element.

19. A method of operating an aerosol delivery device to control an operating mode comprising:

detecting, using a motion sensor arranged to detect motion of the device and to output corresponding motion detection signals to control circuitry and an airflow sensor arranged to detect a flow of air in the device and to output corresponding airflow detection signals to the control circuitry, when there is a predefined sequence of events comprising at least one tapping event and at least one airflow event; and in response to the detecting, switching the device from a first operating mode to a second operating mode.

20. An aerosol delivery device comprising:

control means for controlling an operating mode of the device;

motion sensor means for detecting motion of the device and for outputting corresponding motion detection signals to the control means; and airflow sensor means for detecting a flow of air in the device and for outputting corresponding airflow detection signals to the control means;

wherein the control means is configured to determine from the motion detection signals when there is a tapping event corresponding to the device being tapped by a user and to determine from the airflow detection signals when there is an airflow event corresponding a flow of air in the device, and wherein the control means is configured to control the device to switch from a first operating mode to a second operating mode in response to the detection of a predefined sequence of events comprising at least one tapping event and at least one airflow event.

21. An aerosol delivery device comprising:

a control element for controlling operation of the device;

a motion sensor for detecting when a user taps the device and outputting a motion detection signal to the control element in response thereto; and an airflow sensor for detecting when a user inhales or blows through the device and outputting an airflow detection signal to the control element in response thereto, wherein the control element is configured to control an operating characteristic of the device in response to a predefined sequence of detection signals comprising at least one motion detection signal and at least one airflow detection signal being received by the control element.

* * * * *